United States Patent [19]
Kim et al.

[11] Patent Number: 5,776,965
[45] Date of Patent: Jul. 7, 1998

[54] PROPENOIC ESTER DERIVATIVES HAVING 4-HYDROXYPYRAZOLE GROUP AND THE USE THEREOF

[75] Inventors: Sung Soo Kim; Byung Sup Kim; Ki Jun Hwang, all of Daejeon, Rep. of Korea

[73] Assignee: Korea Research Institute of Chemical Technology, Rep. of Korea

[21] Appl. No.: 702,634

[22] PCT Filed: Mar. 14, 1995

[86] PCT No.: PCT/KR95/00020

§ 371 Date: Nov. 1, 1996

§ 102(e) Date: Nov. 1, 1996

[87] PCT Pub. No.: WO95/25095

PCT Pub. Date: Sep. 21, 1995

[30] Foreign Application Priority Data

Mar. 15, 1994 [KR] Rep. of Korea ............... 1994-5088

[51] Int. Cl.$^6$ ..................... A01N 43/56; C07D 231/18
[52] U.S. Cl. ................. 514/407; 548/366.7; 548/367.1; 548/368.1; 548/370.1; 548/370.4
[58] Field of Search ............... 548/366.7, 367.1, 548/368.1, 370.1, 370.4; 502/282; 514/407

[56] References Cited

U.S. PATENT DOCUMENTS

| | | | |
|---|---|---|---|
| 4,957,937 | 9/1990 | Schuetz et al. | 514/407 |
| 4,994,495 | 2/1991 | Clough et al. | 514/574 |
| 5,003,101 | 3/1991 | Brand et al. | 560/104 |
| 5,021,581 | 6/1991 | Clough et al. | 546/309 |
| 5,157,101 | 10/1992 | Schuetz et al. | 514/269 |
| 5,366,984 | 11/1994 | Schuetz et al. | 548/376.1 X |
| 5,374,644 | 12/1994 | Clough et al. | 514/407 X |
| 5,538,940 | 7/1996 | Sauter et al. | 504/282 X |

FOREIGN PATENT DOCUMENTS

| | | |
|---|---|---|
| 422597A | 4/1991 | European Pat. Off. |
| 460575B | 12/1991 | European Pat. Off. |
| 472300A | 2/1992 | European Pat. Off. |
| 94/00436 | 1/1994 | WIPO |

OTHER PUBLICATIONS

K. Yamada, et al., "New Methods for α-Methylenation of γ-Butyrolactones," Tetrahedron Letters, No. 29 (1973), pp. 2745–2746.
G.N. Vyas et al., "Quinacetopheonone Monomethyl Ether," Organic Syntheses, Collective vol. 4 (1963), pp. 836–838.
S.K. Dubey et al., "Synthesis of Dihydro Diols and Diol Epoxides of Benzo[f]quinoline," The Journal of Organic Chemistry, vol. 51, No. 18 (1986), pp. 3407–3412.
S. Iwata et al., "Synthesis of 4–Hydroxy–3–trifluoromethylpyrazoles," Journal of Heterocyclic Chemistry, vol. 28, No. 8 (1991), pp. 1971–1976.
P.J. Fagan et al., "Cycloadditions and other Chemistry of 4–oxygenated Pyrazoles," Canadian Journal of Chemistry, vol. 57, No. 8 (1979), pp. 904–912.
M. Rambaud et al., "A One–Step Synthesis of Alkyl 2–Oxo–3–alkenoates from Alkenyl Grignard Reagents and Dialkyl Oxalates," Synthesis: Journal of Synthetic Organic Chemistry, (1988), pp. 564–566.

Primary Examiner—Fiona T. Powers
Attorney, Agent, or Firm—Finnegan, Henderson, Farabow, Garrett & Dunner, L.L.P.

[57] ABSTRACT

The present invention relates to novel propenoic ester derivatives having 4-hydroxypyrazole group of formula (I) which have active fungicidal properties, wherein $R^1$ represents hydrogen, halogen, nitro, an alkyl group having 1 to 6 carbon atoms, or an alkoxy group having 1 to 6 carbon atoms; $R^2$ represents an alkoxy group having 1 to 6 carbon atoms, a haloalkoxy group having 1 to 6 carbon atoms, or an alkylthio group having 1 to 6 carbon atoms; $R^3$ represents an alkyl group having 1 to 6 carbon atoms, an allyl group, a benzyl group, a phenyl group, or a substituted phenyl group by substituent selected from the group consisting of an alkyl group having 1 to 6 carbon atoms, an alkoxy group having 1 to 6 carbon atoms, nitro and [0a8]alogen; $R^4$ represents hydrogen, halogen, an alkyl group having 1 to 6 carbon atoms, a phenyl group, or a substituted phenyl group by substituent selected from the group consisting of an alkyl group having 1 to 6 carbon atoms, an alkoxy group having 1 to 6 carbon atoms, nitro and halogen; $R^5$ represents hydrogen, halogen, a haloalkyl group, an alkyl group having 1 to 6 carbon atoms, a phenyl group, or a substituted phenyl group by substituent selected from the group consisting of an alkyl group having 1 to 6 carbon atoms, an alkoxy group having 1 to 6 carbon atoms, nitro and halogen; and X represents carbon or nitrogen.

8 Claims, No Drawings

PROPENOIC ESTER DERIVATIVES HAVING 4-HYDROXYPYRAZOLE GROUP AND THE USE THEREOF

BACKGROUND OF THE INVENTION

1. Technical Field

The present invention relates to novel propenoic ester derivatives having a 4-hydroxypyrazole group of the following formula(I) which have active fungicidal properties.

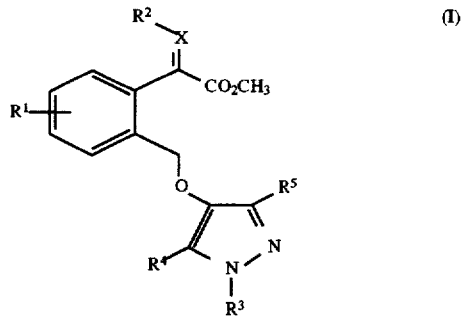

wherein:
- $R^1$ represents hydrogen, halogen, nitro, an alkyl group having 1 to 6 carbon atoms, or an alkoxy group having 1 to 6 carbon atoms;
- $R^2$ represents an alkoxy group having 1 to 6 carbon atoms, a haloalkoxy group having 1 to 6 carbon atoms, or an alkylthio group having 1 to 6 carbon atoms;
- $R^3$ represents an alkyl group having 1 to 6 carbon atoms, an allyl group, a benzyl group, a phenyl group, or a substituted phenyl group which is substituted by a substituent selected from the group consisting of an alkyl group having 1 to 6 carbon atoms, an alkoxy group having 1 to 6 carbon atoms, nitro and halogen;
- $R^4$ represents hydrogen, halogen, an alkyl group having 1 to 6 carbon atoms, a phenyl group, or a substituted phenyl group which is substituted by a substituent selected from the group consisting of an alkyl group having 1 to 6 carbon atoms, an alkoxy group having 1 to 6 carbon atoms, nitro and halogen,
- $R^5$ represents hydrogen, halogen, a haloalkyl group, an alkyl group having 1 to 6 carbon atoms, a phenyl group, or a substituted phenyl group which is substituted by a substituent selected from the group consisting of an alkyl group having 1 to 6 carbon atoms, an alkoxy group having 1 to 6 carbon atoms, nitro and halogen; and X represents a CH group or nitrogen.

2. DESCRIPTION OF THE PRIOR ART

Even though the known fungicides possess excellent fungicidal properties, the development of compounds based upon a similar basic structure has given rise to the problem of resistance development by the target fungi due to long exposure to these compounds with a common basic structure.

As a result of a continuous effort to solve this problem, a series of novel propenoic ester derivatives was disclosed firstly in European Patent No. 472300 of ICI Co., U.S. Pat. No. 4994495, European Patent No. 422597 of BASF Co., U.S. Pat. No. 5003101 and European Patent No. 460575 of Ciba-Geigy Co., but the fungicidal activity of the reported compounds was too low and limited in its application therefore, there is a need for potent fungicides which possess effective fungicidal activity, low toxicity and good economy.

Therefore, in consideration of the aforesaid points, the present inventors have made efforts to develop new fungicidal compounds which have powerful fungicidal activities to various target fungi and low toxicity, we have applied for a patent about propenoic ester derivatives having a pyrazole group and the use thereof (Korean laid-open patent No. 94-432, PCT/KR93/00052).

As the result, the inventors of the present invention synthesized novel propenoic ester derivatives by using 4-hydroxypyrazole compounds which have not been so far known.

SUMMARY OF THE INVENTION

The objective of the present invention is to provide novel propenoic ester derivatives with strong fungicidal activities toward various fungi and broad fungicidal spectrum and a simple manufacturing process.

Another objective is to provide fungicidal compositions containing the derivatives as an active compound.

DETAILED DESCRIPTION OF THE INVENTION

The present invention is identified as propenoic ester derivatives having 4-hydroxypyrazole group which correspond to the following formula(I), and agricultural preparations containing compounds of formula(I) as an active ingredient:

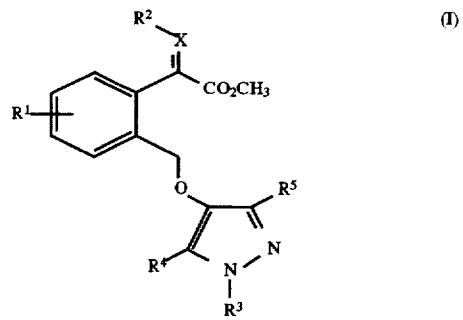

In formula (I), $R^1$, $R^2$, $R^3$, $R^4$, $R^5$ and X are respectively defined as above.

In the formula(I) according to the present invention, the preferred derivatives with greatest fungicidal activities are those where $R^1$ and $R^4$ represent hydrogen, $R^2$ represents a methyl or methylthio group, $R^3$ represents a phenyl or substituted phenyl group which is substituted by a substituent selected from the group consisting of an alkyl group having 1 to 6 carbon atoms, and an alkoxy group having 1 to 6 carbon atoms, and $R^5$ represents a trifluoromethyl or methyl group.

According to the present invention, propenoic ester derivatives of the above formula(I) can be prepared by the following two methods.

As shown in the following reaction pathway 1, the first method is the preparation of propenoic ester derivatives of the above formula(I) by reacting propenoic benzyl bromide of the following formula(II) with 4-hydroxypyrazole of the following formula(III) in the presence of an appropriate base.

[Reaction Pathway 1]

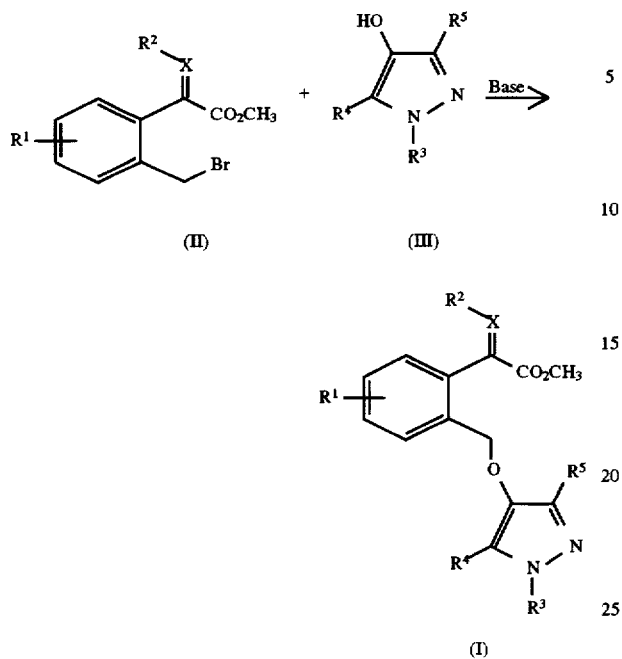

In the above formulas(II) and (III), $R^1, R^2, R^3, R^4, R^5$, and X are respectively defined as above.

In the above reaction, the compounds of formula(II) are reacted with the same mole of the compound of formula(III) in the presence of 1-3 equivalents of base.

Additionally in the above reaction, an organic solvent such as chlorobenzene, tetrahydrofuran, dimethylformamide or dichloroethane and base such as potassium carbonate, sodium hydride, triethylamine or pyridine may be used. The completion of the reaction for obtaining the compound of formula(I) is when no more compound of formula(II) remains, and it can be easily checked by T.L.C.

The compounds of formula(II) and formula(III) in the above reaction pathway can be easily prepared by the well known reaction pathway that formylation, alkylation and bromination using substituted o-tolylacetic acid as starting material [Reference: The compound of formula(II); 1. K. Yamada, M. Kato and Y. Hirata, Tetrahedron Lett., 2745 (1973). 2. G. N. Vyas and N. M. Shah, Org. Syn., Coll. Vol., 4, 836(1963). 3. S. K. Dubey and S. Kumar, J. Org. Chem., 51, 3407(1986). The compound of formula (III); 1. S. Iwata, J. Namekata, K. Tanaka and K. Mitsuhashi, J. Het Chem., 28, 1971(1991). 2. P. J. Fagan, E. E. Neidert, M. J. Nye, M. J. Ohare and W. Tang, Can. J. Chem., 57, 904(1979)].

As shown in the following reaction pathway 2, the second method is the preparation of propenoic ester derivatives of the above formula(I) by reacting the glyoxylate derivatives of the following formula (IV) with alkoxymethyl triphenyl phosphine, alkylthiomethyl triphenyl phosphine or alkoxylamine, respectively.

[Reaction Pathway 2.]

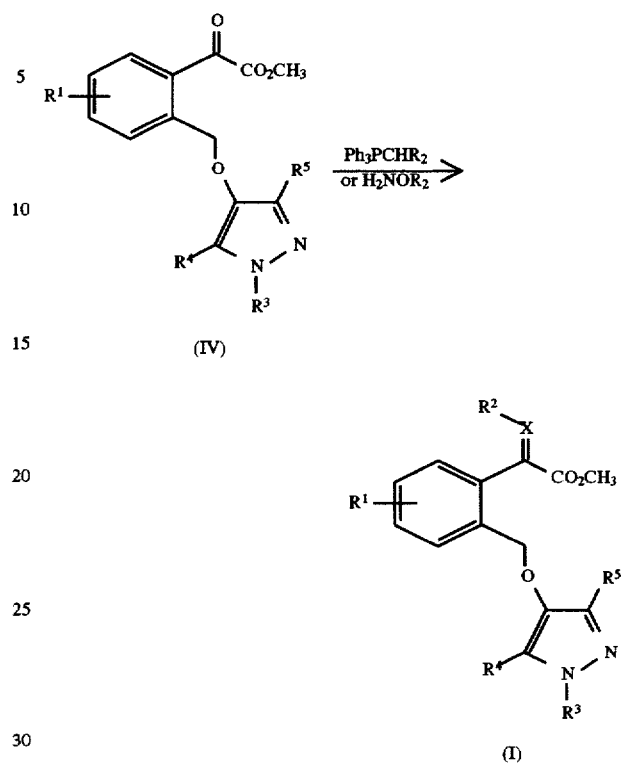

In the above formulas, $R^1, R^2, R^3, R^4, R^5$, and X are respectively defined as above.

In the above reaction, alkoxymethyl triphenyl phosphine, alkylthiomethyl triphenyl phosphine or alkoxylamine is reacted with the 1-5 equivalents of the compound of formula (IV).

In the case of the reaction of alkoxy methyl triphenyl phosphine or alkylthiomethyl triphenylphosphine, tetrahydrofuran or diethyl ether can be used as an organic solvent. In the case of the reaction of alkoxylamine, dichloromethane, 1,2-dichloroethane, ethyl alcohol or pyridine are desirable to be used as an organic solvent. The completion of reaction is realized when the compound of formula(IV) no longer remains in the reaction, and it can be easily checked by T.L.C.

The compound of formula(IV) in the above reaction can be easily prepared by the well known reaction pathway, that is, oxalation, bromination and pyrazole condensation using 2-bromotoluene as a starting material [Reference: 1. M. Ranbaud, M. Bakasse, C. T. Duguay and J. Villieras, Synthesis, 564(1988). 2. S. K. Dubey and S. Kumar, J. Org. Chem., 51, 3407(1986)].

The compound of the above formula(I) which is prepared by the above reactions consists of cis or tans stereoisomers according to the steric position of $R^2$ about the double bond.

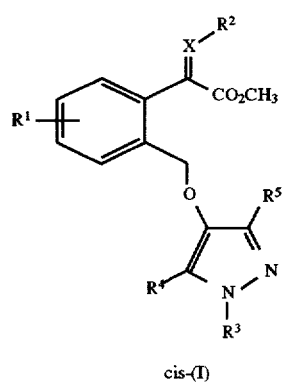

cis-(I)

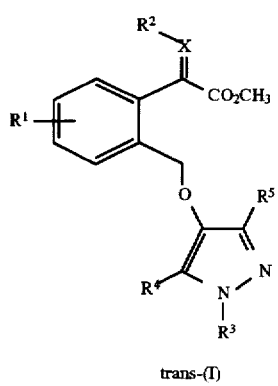

trans-(I)

The reaction pathway 2, gave a mixture of trans-(I) compound as major product and cis-(I) compound as minor product.

The fungicidal activities of the compound(I) according to the present invention were tested for a mixture of isomers as well as individual isolated isomers when isolation was possible.

New propenoic ester derivatives of formula (I) are listed in the following Table 1.

TABLE 1

| Comp. No. | $R^1$ | $R^2$ | $R^3$ | $R^4$ | $R^5$ | X |
|---|---|---|---|---|---|---|
| 1 | H | $CH_3O$ | $CH_3$ | H | $CF_3$ | trans-CH |
| 2 | H | $CH_3O$ | $CH_3$ | H | $CF_3$ | cis-CH |
| 3 | H | $CH_3O$ | $CH_3$ | H | $CF_3$ | trans-N |
| 4 | H | $CH_3O$ | $C_2H_5$ | H | $CF_3$ | CH |
| 5 | H | $CH_3O$ | $i$-$C_3H_7$ | H | $CF_3$ | CH |
| 6 | H | $CH_3O$ | $t$-$C_4H_9$ | H | $CF_3$ | CH |
| 7 | H | $CH_3O$ | $CH_2CH=CH_2$ | H | $CF_3$ | CH |
| 8 | H | $CH_3O$ | $C_6H_5$ | H | $CF_3$ | trans-CH |
| 9 | H | $CH_3O$ | $C_6H_5$ | H | $CF_3$ | cis-CH |
| 10 | H | $CH_3O$ | $C_6H_5$ | H | $CF_3$ | cis-N |
| 11 | H | $CH_3O$ | $C_6H_5$ | H | $CF_3$ | trans-N |
| 12 | H | $CH_3O$ | $C_6H_5$ | H | $CHF_2$ | CH |
| 13 | H | $CH_3O$ | $C_6H_5$ | H | $CH_2F$ | CH |
| 14 | H | $CH_3O$ | $C_6H_5$ | H | $CH_3$ | trans-CH |
| 15 | H | $CH_3O$ | $C_6H_5$ | H | $CH_3$ | trans-N |
| 16 | H | $CH_3O$ | $C_6H_5$ | H | H | CH |
| 17 | H | $CH_3O$ | $C_6H_5$ | H | Cl | CH |
| 18 | H | $CH_3O$ | $C_6H_5$ | H | $C_2H_5$ | CH |
| 19 | H | $CH_3O$ | $C_6H_5$ | H | $C_6H_5$ | CH |
| 20 | H | $CH_3O$ | $C_6H_5$ | Cl | $CF_3$ | CH |
| 21 | H | $CH_3O$ | $C_6H_5$ | F | $CF_3$ | CH |
| 22 | H | $CH_3O$ | $C_6H_5$ | $CH_3$ | $CF_3$ | CH |
| 23 | H | $CH_3O$ | $C_6H_5$ | $CH_3$ | $CF_3$ | N |
| 24 | H | $CH_3O$ | $C_6H_5$ | $C_2H_5$ | $CF_3$ | CH |
| 25 | H | $CH_3O$ | $C_6H_5$ | $i$-$C_3H_7$ | $CF_3$ | CH |
| 26 | H | $CH_3O$ | $C_6H_5$ | $C_6H_5$ | $CF_3$ | CH |
| 27 | H | $CH_3O$ | 4-$CH_3$-$C_6H_4$ | H | $CF_3$ | CH |
| 28 | H | $CH_3O$ | 4-$CH_3$-$C_6H_4$ | H | $CF_3$ | N |
| 29 | H | $CH_3O$ | 4-$CH_3$-$C_6H_4$ | H | $CH_3$ | CH |
| 30 | H | $CH_3O$ | 3-$CH_3$-$C_6H_4$ | H | $CF_3$ | CH |

TABLE 1-continued

| Comp. No. | R¹ | R² | R³ | R⁴ | R⁵ | X |
|---|---|---|---|---|---|---|
| 31 | H | CH₃O | 3-methylphenyl | H | CF₃ | N |
| 32 | H | CH₃O | 3-methylphenyl | H | CH₃ | CH |
| 33 | H | CH₃O | 4-methoxyphenyl | H | CF₃ | CH |
| 34 | H | CH₃O | 4-methoxyphenyl | H | CF₃ | N |
| 35 | H | CH₃O | 4-methoxyphenyl | H | CH₃ | CH |
| 36 | H | CH₃O | 4-nitrophenyl | H | CF₃ | CH |
| 37 | H | CH₃O | 4-nitrophenyl | H | CF₃ | N |
| 38 | H | CH₃O | 4-nitrophenyl | H | CH₃ | CH |
| 39 | H | CH₃O | 4-chlorophenyl | H | CF₃ | CH |
| 40 | H | CH₃O | 4-chlorophenyl | H | CF₃ | N |
| 41 | H | CH₃O | 4-chlorophenyl | H | CH₃ | CH |
| 42 | H | CH₃O | 2-chlorophenyl | H | CF₃ | CH |
| 43 | H | CH₃O | 2-chlorophenyl | H | CF₃ | N |

TABLE 1-continued
| Comp. No. | R¹ | R² | R³ | R⁴ | R⁵ | X |
|---|---|---|---|---|---|---|
| 44 | H | CH₃O | 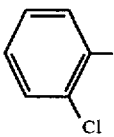 2-Cl-C₆H₄ | H | CH₃ | CH |
| 45 | H | CH₃O | 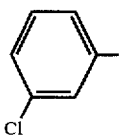 3-Cl-C₆H₄ | H | CF₃ | CH |
| 46 | H | CH₃O | 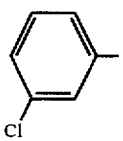 3-Cl-C₆H₄ | H | CF₃ | N |
| 47 | H | CH₃O | 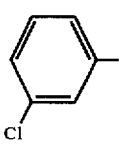 3-Cl-C₆H₄ | H | CH₃ | CH |
| 48 | H | CH₃O | 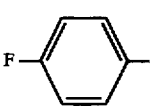 4-F-C₆H₄ | H | CF₃ | CH |
| 49 | H | CH₃O | 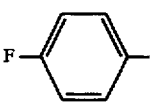 4-F-C₆H₄ | H | CF₃ | N |
| 50 | H | CH₃O | 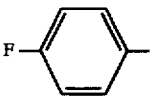 4-F-C₆H₄ | H | CH₃ | CH |
| 51 | H | CH₃O | 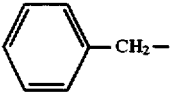 C₆H₅CH₂— | H | CF₃ | CH |
| 52 | H | CH₃O | 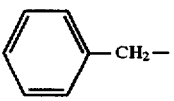 C₆H₅CH₂— | H | CF₃ | N |
| 53 | H | CH₃O | 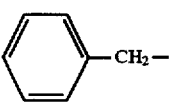 C₆H₅CH₂— | H | CH₃ | CH |
| 54 | H | CH₃S | C₆H₅ | H | CF₃ | trans-CH |
| 55 | H | CH₃S | C₆H₅ | H | CH₃ | CH |
| 56 | H | CH₃S | 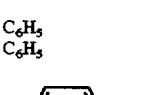 3-CH₃-C₆H₄ | H | CF₃ | CH |
| 57 | H | CH₃S | 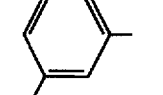 3-CH₃-C₆H₄ | H | CH₃ | CH |

TABLE 1-continued

| Comp. No. | R¹ | R² | R³ | R⁴ | R⁵ | X |
|---|---|---|---|---|---|---|
| 58 | H | $CH_3S$ | 4-$CH_3$-$C_6H_4$- | H | $CF_3$ | CH |
| 59 | H | $CH_3S$ | 4-$CH_3$-$C_6H_4$- | H | $CH_3$ | CH |
| 60 | H | $CH_3S$ | 4-$CH_3O$-$C_6H_4$- | H | $CF_3$ | CH |
| 61 | H | $CH_3S$ | 4-$CH_3O$-$C_6H_4$- | H | $CH_3$ | CH |
| 62 | H | $CH_3S$ | 4-Cl-$C_6H_4$- | H | $CF_3$ | CH |
| 63 | H | $CH_3S$ | 4-Cl-$C_6H_4$- | H | $CH_3$ | CH |
| 64 | H | $CH_3S$ | 3-Cl-$C_6H_4$- | H | $CF_3$ | CH |
| 65 | H | $CH_3S$ | 4-F-$C_6H_4$- | H | $CF_3$ | CH |
| 66 | H | $CH_3S$ | 4-$NO_2$-$C_6H_4$- | H | $CF_3$ | CH |
| 67 | H | $CH_3S$ | 4-$NO_2$-$C_6H_4$- | H | $CH_3$ | CH |
| 68 | H | $CH_3S$ | $CH_3$ | H | $CF_3$ | CH |
| 69 | H | $C_2H_5O$ | $CH_3$ | H | $CF_3$ | CH |
| 70 | H | $C_2H_5O$ | $C_6H_5$ | H | $CF_3$ | CH |
| 71 | H | $C_2H_5O$ | $C_6H_5$ | H | $CF_3$ | N |
| 72 | H | $C_2H_5S$ | $C_6H_5$ | H | $CF_3$ | CH |
| 73 | H | $CHF_2O$ | $C_6H_5$ | H | $CF_3$ | CH |
| 74 | 4-Cl | $CF_3CH_2O$ | $C_6H_5$ | H | $CF_3$ | CH |
| 75 | 4-Cl | $CH_3O$ | $C_6H_5$ | H | $CF_3$ | CH |
| 76 | 4-Cl | $CH_3O$ | $C_6H_5$ | H | $CF_3$ | N |
| 77 | 4-Cl | $CH_3O$ | $C_6H_5$ | H | $CH_3$ | CH |
| 78 | 4-Cl | $CH_3O$ | $CH_3$ | H | $CF_3$ | CH |
| 79 | 4-Cl | $CH_3S$ | $C_6H_5$ | H | $CF_3$ | CH |
| 80 | 3-Cl | $CH_3O$ | $C_6H_5$ | H | $CF_3$ | CH |
| 81 | 3-Cl | $CH_3O$ | $C_6H_5$ | H | $CF_3$ | N |
| 82 | 3-Cl | $CH_3O$ | $C_6H_5$ | H | $CH_3$ | CH |
| 83 | 3-Cl | $CH_3O$ | $CH_3$ | H | $CF_3$ | CH |
| 84 | 3,4-$Cl_2$ | $CH_3O$ | $C_6H_5$ | H | $CF_3$ | CH |
| 85 | 4-$CH_3$ | $CH_3O$ | $C_6H_5$ | H | $CF_3$ | CH |
| 86 | 4-$CH_3$ | $CH_3O$ | $C_6H_5$ | H | $CF_3$ | N |
| 87 | 4-$CH_3$ | $CH_3O$ | $C_6H_5$ | H | $CH_3$ | CH |
| 88 | 4-$CH_3$ | $CH_3O$ | $CH_3$ | H | $CF_3$ | CH |
| 89 | 4-$CH_3O$ | $CH_3O$ | $C_6H_5$ | H | $CF_3$ | CH |

TABLE 1-continued

| Comp. No. | R$^1$ | R$^2$ | R$^3$ | R$^4$ | R$^5$ | X |
|---|---|---|---|---|---|---|
| 90 | 4-CH$_3$O | CH$_3$O | C$_6$H$_5$ | H | CF$_3$ | N |
| 91 | 4-CH$_3$O | CH$_3$O | C$_6$H$_5$ | H | CH$_3$ | CH |
| 92 | 4-CH$_3$O | CH$_3$O | CH$_3$ | H | CF$_3$ | CH |
| 93 | 4-C$_2$H$_5$ | CH$_3$O | C$_6$H$_5$ | H | CF$_3$ | CH |
| 94 | 4-C$_2$H$_5$ | CH$_3$O | C$_6$H$_5$ | H | CF$_3$ | N |
| 95 | 4-NO$_2$ | CH$_3$O | C$_6$H$_5$ | H | CF$_3$ | CH |
| 96 | 4-NO$_2$ | CH$_3$O | C$_6$H$_5$ | H | CF$_3$ | N |
| 97 | 4-NO$_2$ | CH$_3$O | C$_6$H$_5$ | H | CH$_3$ | CH |
| 98 | 4-NO$_2$ | CH$_3$O | CH$_3$ | H | CF$_3$ | CH |

The following examples more fully illustrate the present invention, but the invention is not intended to he limited thereby.

EXAMPLE 1 trans-Methyl-2-[2-(1-methyl-3-trifluoromethyl-4-pyrazoyl)-methyl- phenyl]-3-methoxy propenoate (Comp. No. 1)

To a solution of methyl-2-(2-bromomethylphenyl)-3-methoxypropenoate (511 mg, 1.8 mmol) in dimethylformamide (6 ml) at room temperature was added 1-methyl-3-trifluoromethyl-4-hydroxypyrazole (300 mg, 1.8 mmol) and potassium carbonate (345 mg, 2.5 mmol) After being stirred for 15 h at room temperature, the reaction mixture was quenched by addition of diethyl ether (15 ml) and water (20 ml). The aqueous layer was extracted with dimethyl ether. The combined organic extracts were washed with water (10 ml×3), dried over anhydrous magnesium sulfate, filtered and concentrated under reduced pressure to afford crude product. Final purification was effected by silica-gel column chromatography (ethyl acetate/hexane, 2/1) to afford the Comp. No. 1 (271 mg, 51% yield).
$^1$H NMR (CDCl$_3$): δ 3.65(s, 3 H), 3.68(s, 3 H), 3.74(s, 3 H), 4.83(s, 2 H), 6.88(s, 1 H), 7.09–7.48(m, 4 H), 7.54(s, 1 H).
m/e: 371(M$^+$)

EXAMPLE 2 trans-Methyl-2-[2-(1-phenyl-3-trifluoromethyl-4-pyrazoyl)-methyl-phenyl]-3-methoxy propenoate (Comp. No. 8)

To a solution of methyl-2-(2-bromomethylphenyl)-3-methoxypropenoate (397 mg, 1.4 mmol) in dimethylformamide (5 ml) at room temperature was added 1-phenyl-3-trifluoromethyl-4-hydroxypyrazole (320 mg, 1.4 mmol) and potassium carbonate (276 mg, 2.0 mmol). After being stirred for 15 h at room temperature, the reaction mixture was quenched by addition of diethyl ether (15 ml) and water (20 ml). The aqueous layer was extracted with diethyl ether. The combined organic extracts were washed with water (10 ml×3), dried over anhydrous magnesium sulfate, filtered and concentrated under reduced pressure to afford crude product. Final purification was effected by silica-gel column chromatography (ethyl acetate/hexane, 1/3) to afford the Comp. No. 8. (460 mg, 77% yield).
$^1$H NMR (CDCl$_3$): δ 3.68(s, 3 H), 3.77(s, 3 H), 4.96(s, 2 H), 7.15–7.62(m, 9 H), 7.61 (s, 1H).
m/e: 433(M$^+$)

EXAMPLE 3 cis-Methyl 2-[2-(1-phenyl-3-trifluoromethyl-4-pyrazoyl)-methyl-phenyl]glyoxylate methyloxime (Comp. No. 10)
trans-Methyl-2-[2-(1-phenyl-3-trifluoromethyl-4-pyrazoyl)-methyl-phenyl]glyoxylate methyloxime (Comp. No. 11).

To a solution of methyl-2-[2-(1-phenyl-3-trifluoromethyl-4-pyrazoyl)-3-methyl-phenyl] glyoxylate (230 mg, 0.6 mmol) in methanol (5 ml) at room temperature was added methoxylamine hydrochloride (200 mg, 2.5 mmol) and pyridine (243 µl, 3 mmol) and then heated to 70° C. After being stirred for 12h at 70° C., the reaction mixture was concentrated under reduced pressure, and diluted with dichloromethane (15 ml) and water (10ml). The aqueous layer was extracted with dichloromethane. The combined organic extracts were washed with brine, dried over anhydrous magnesium sulfate, filtered and concentrated under reduced pressure to afford crude product. Final purification was effected by silica-gel column chromatography (ethyl acetate/hexane, 1/3) to afford the Comp. No. 10 (100 mg, 38% yield) and Comp. No 11 (110 mg, 43% yield).
Comp. No. 10.
$^1$H NMR (CDCl$_3$): δ 3.92(s, 3 H), 4.07(s, 3 H), 5.33(s, 2 H), 7.15–7.99(m, 9 H).
m/e: 434(M$^+$)
R$_f$: 0.49(ethyl acetate/hexane, 1/3)
Comp. No. 11.
$^1$H NMR (CDCl$_3$): δ 3.89(s, 3 H), 4.03(s, 3 H), 4.98(s, 2 H), 7.10–7.93(m, 9 H).
m/e: 434(M$^+$)
R$_f$: 0.37(ethyl acetate/hexane, 1/3)

EXAMPLE 4 trans-Methyl-2-[2(1-phenyl-3-methyl-4-pyrazoyl)-methyl-phenyl]-3-methoxypropenoate (Comp. No. 14).

To a solution of methyl-2-(2-bromomethylphenyl)-3-methoxypropenoate (420 mg, 1.5 mmol) in dimediylformamide (6 ml) at room temperature was added 1-phenyl-3-methyl-4-hydroxypyrazole (270 mg, 1.5 mmol) and potassium carbonate (276 mg, 2.0 mmol). After being stirred for 24 h at room temperature, the reaction mixture was quenched by addition of diethyl ether (15 ml) and water (20 ml). The aqueous layer was extracted with diethyl ether. The combined organic extracts were washed with water (10 ml×3), dried over anhydrous magnesium sulfate, filtered and concentrated under reduced pressure to afford crude product. Final purification was effected by silica-gel column chromatography (ethyl acetate/hexane, 1/3) to afford the Comp. No. 14. (170 mg, 31% yield).
$^1$H NMR (CDCl$_3$): δ 2.25(s, 3 H), 3.83(s, 3 H), 3.99(s, 3 H), 5.20(s, 2 H), 7.10–7.15(m, 9 H), 7.82(S, 1 H).
m/e: 379(M$^+$)

EXAMPLE 5 trans-Methyl-2-[2-(1-phenyl-3-trifluoromethyl-4-pyrazoyl)-methyl-phenyl]-3-methylthio propenoate (Comp. No. 54).

To a solution of methylthiomethyltriphenylphosphonium chloride (358 mg, 1 mmol) in tetrahydrofuran (5 ml) at −78°

C. was added dropwise n-butyl lithium (2.5M in n-hexane, 460 μl, 1.15 mmol). After being stirred for 1 h at −78° C., a solution of methyl-2-[2-(1-phenyl-3-trifluoromethyl-4-pyrazoyl)-methyl-phenyl]glyoxylate (450 mg, 1 mmol) in tetrahydrofuran (3 ml) was added dropwise over 10 minute at −78° C. to the reaction mixture. After warming up to −10° C., the reaction was allowed to proceed for 5 h at −10° C., and then quenched by addition of water (20 ml). The aqueous layer was extracted with diethyl ether (15 ml×3) .The combined organic extracts were washed with brine, dried over anhydrous magnesium sulfate, filtered and concentrated under reduced pressure to afford crude product. Final purification was effected by silica-gel column chromatography (ethylacetate/hexane, 1/5) to afford the Comp. No. 54 (342 mg, 67% yield).

$^1$H NMR (CDCl$_3$): δ 2.41(s, 3 H), 3.75 (s, 3 H), 5.02(s, 2 H), 7.15~7.90(m, 9 H), 7.95 (s, 1 H).

m/e: 449(M$^+$)

The present invention is directed to the fungicidal compositions comprising the fungicidal compound of the present invention as an active compound. The fungicidal compositions can be formulated in various forms such as aqueous dispersions, emulsions, dusts, granules and so forth. These compositions are preferred to comprise one or more active compounds of the present invention with one or more suitable adjuvants such as carries and diluents which are chemically inert to the active compound.

Tile exact concentration of Lee active compound in a composition thereof with an adjuvant therefor can vary; it is only necessary that the active compounds be present in sufficient amounts so as to make possible the application of a fungicidally effective dosage.

For example, in the case that the compositions are emulsions or aqueous dispersions, the amount of the active compound is preferred to range from 10 to 90% by weight And in the case of dust compositions, the amount is preferred to range from 0.1 to 30% by weight, also in die case of granule compositions, the amount is preferred to range from 1 to 30% by weight. But, the amount of the active compound in the compositions is somewhat variable according to the proposed use of the compositions.

Preferred carriers which are employed in the compositions according to the present invention are liquid carriers which are selected from alcohols(i.e. monohydric alcohols like methanol, dihydric alcohols like ethylene glycol, and trihydric alcohols like glycerine, etc.), ketones(i.e. acetone, methylethylketone, etc), ethers(i.e. dioxane, tetrahydrofuran, cellosolve, etc.), aliphatic hydrocarbons (i.e. gasoline, kerosene, etc.), hydrocarbon halides(i.e. chloroform, carbon tetrachloride, etc.), acid amides(i.e. dimethylformamide, etc.), esters(i.e butyl acetate, ethyl acetate, glyceride, etc.), and nitriles(i.e. aectonitrile, etc.), and solid carriers which are selected from mineral compounds such as kaoline, clay, bentonite, acid clay, talc, diatomaceous earth, silica and sand, and vegetable powders such as arbor. The above noted liquid carriers can be used separately or in company with one or more other liquid carriers.

The fungicidal composition of the present invention may include emulsifying agents spreaders, dispersing agents or permeating agents. Also, the composition may include nonionic, anionic or cationic surfactants, for example, fatty acid soda or polyoxyalkyl esters, alkyl sulfonates or polyethylene glycolethers.

On the other hand, one of the compounds of the present invention or compositions containing the same, can be advantageously employed in combination with one or more additional known pesticidal compounds which are active agricultural chemical. Such additional pesticidal compounds may be insecticides, herbicides, plant hormones and sterilizers, and if necessary, fertilizers.

Composition 1 (Emulsion)

| Comp. No. 1 | 20% (by weight) |
|---|---|
| xylene | 75% |
| polyoxyethylen glycolether | 5% |

The foregoing components were mixed to form an emulsion composition.

Composition 2 (Dusts)

| Comp. No. 8 | 5% (by weight) |
|---|---|
| kaoline | 94.6% |
| silicon (antifoaming agent) | 0.3% |
| polyoxyethylene glycolether | 0.1% |

The foregoing components were mixed to form a dust composition.

Composition 3 (Agueous dispersion)

| Comp. No. 11 | 30% (by weight) |
|---|---|
| sodium lignosulfonate | 5% |
| polyoxyethylene glycolether | 5% |
| bentonite | 60% |

The foregoing components were mixed to form an aqueous dispersion composition.

Composition 4 (Granules)

| Comp. No. 54 | 10% (by weight) |
|---|---|
| sodium lignosulfonate | 5% |
| bentonite | 85% |

The foregoing components were kneaded using with water and formed into a granule composition.

The superior fungicidal activities of propenoic ester derivatives(I) according to the present invention prepared by die above examples were tested to check protective effect against the barley powdery mildew, the wheat leat rust, the rice blast and rice sheath blight. A 10% acetone solution containing the compound(I) was diluted using a Tween-20 solution of 250 ppm strength(500 ppm in the case of rice). 500 ml of this chemical solution was sprayed to plants of equal height and allowed on to stand at room temperature for 24 hours. After evaporation of the spray solution and water, the test plants were inoculated with target fungi. The tests were carried out two times by the same method.

In the case of a fungicidal rate of 100%, the concentration of the test chemicals was gradually reduced until the EC$_{50}$ value, namely the concentration (ppm) which gives a fungicidal rate of 50% was determined.

TEST 1

Fungicidal Test for Rice Blast (RCB)

*Pyricularia oryzae Cavara* KJ301 as test rice blast fungus was selected and inoculated on rice polish agar medium (Rice polish 20g, Dextrose 10g, Agar 15g, Distilled water 1 l) to incubate at 26° C. for 2 weeks, and then scratched airial mycelia with Rubber Polishman were irradiated with near fluorescent light to form spores at 25°~28° C. for 48 hours.

A suspension of conidia in water(10$^6$ spores/ml) was prepared and sprayed upon the 3~4 leaf stage of rice plants on the foliage. After placing in a dark dew chamber for 24 hours, the treated plants were then held in a lighted growth chamber(26±2° C., 80%) for 5 days, and rated on the disease severity. The disease severity was examined against the percent disease area on the first leaf right under 3~4 leaf stage and compared to the standard rating diagram.

TEST 2
Fungicidal Test for Rice Sheath Blight (RSB)

*Rhizoctonia solani* AG-1 was incubated in wheat bran medium (1 l. bottle), and then the agar disc was inoculated in a growth chamber(27±1° C.) for 7 days.

Rice plans in the 2~7 leaf stage in 5 cm pots were inoculated with the milled conidia. After incubating in a dew chamber(28±1° C.), the disease severity was examined against the percent disease area on the applied leaf of 2~3 leaf stage and compared to the standard rating diagram.

TEST 3
Fungicidal Test for Wheat Leaf Rust (WLR)

Test was made to succession culture of *Puccinia recondita* against the host plants. For the succession culture and the fungicidal effect test, wheats(cultivar; chokwang) were grown in polyvinyl pots(diameter; 6.5 cm) for 7 days, and then spores of the first leaf stage were inoculated.

After placing the treated wheat in a dew chamber at 20° C. for 1 day, the plants were held in a growth chamber (20° C., 70%) for 10 days, and then rated on the disease severity.

The disease severity was examined as the percent disease area after inoculating the spores for 10 days.

TEST 4
Fungicidal Test for Barley Powdery Mildew(BPM)

Tests were made to succession culture of *Eysiphe graminis* &. sp. hordei. For the succession culture and the fungicidal effect tests, barley(Dongbori No. 1) was grown in polyvinyl pots(diameter; 6.5 cm) for 7 days, and then spores of the first leaf stage were inoculated.

The treated barley was held in a growth chamber(22~24° C., 50%), and the disease severity was rated alter 7 days inoculation.

In the above Test 1~4, those compounds which produced a an fungicidal rate of 100% at 500 ppm and, for comparison, commercial fungicidals (controls) were tested according to the method mentioned above, and the $EC_{50}$ values were determined. The results are shown in Table 2.

$EC_{50}$ value means the concentration(ppm) at which a fungicidal rate of 50% is.

The fungicidal rate of the test chemicals was determined according to the following:

Control value (%) =

$$\left( 1 - \frac{\text{Percent of disease area in treatment}}{\text{Percent of disease area in untreated control}} \right) \times 100$$

TABLE 2

The fungicidal rate of the test chemicals ($EC_{50}$, ppm)

| Comp. No. | RCB | RSB | WLR | BPM |
|---|---|---|---|---|
| 1 | 250 | 250 | 10 | 5 |
| 8 | 10 | <2 | <2 | <2 |
| 10 | 10 | 50 | <2 | <2 |
| 11 | <2 | 250 | <2 | <2 |
| 14 | 5 | 50 | <2 | <2 |

TABLE 2-continued

The fungicidal rate of the test chemicals ($EC_{50}$, ppm)

| Comp. No. | RCB | RSB | WLR | BPM |
|---|---|---|---|---|
| 54 | <2 | 250 | <2 | <2 |
| A* | <100 | | <100 | 100 |
| B** | | | 160 | 50 |

(Notes)
RCB (Rice Blast), RSB (Rice Sheath Blight)
WLR (Wheat Leaf Rust), BPM (Barley Powdery Mildew)
A*: Propenoic ester compound disclosed in European Patent No. 472300.
B**: Propenoic ester compound disclosed in European Patent No. 460575.

What is claimed is:

1. A compound of formula (I):

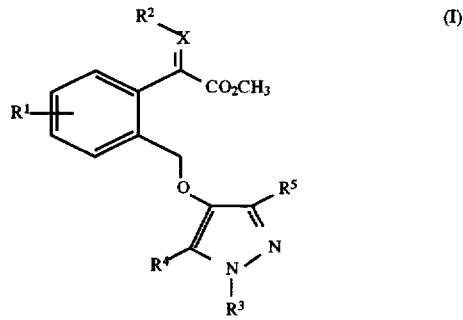

wherein:

$R^1$ represents hydrogen or chlorine;

$R^2$ represents a methoxy group or a methylthio group;

$R^3$ represents a methyl group or a phenyl group;

$R^4$ represents hydrogen or a methyl group;

$R^5$ represents hydrogen a methyl group, or a trifluoromethyl group; and

X represents a CH group or nitrogen.

2. A compound according to claim 1, wherein the compound is a trans stereoisomer.

3. A compound according to claim 1, wherein the compound of formula (I) is trans-methyl-2-[2-(1-phenyl-3-trifluoromethyl-4-pyrazoyl)-methyl-phenyl]-3-methoxy propenoate.

4. A compound according to claim 1, wherein the compound of formula (I) is trans-methyl-2-[2-(1 -phenyl-3-trifluoromethyl-4-pyrazoyl)-methyl-phenyl]glyoxylate methyloxime.

5. A fungicidal composition containing a compound according to claim 1.

6. A fungicidal composition according to claim 5, further including an adjuvant.

7. A fungicidal composition according to claim 6, wherein the adjuvant is a carrier.

8. A fungicidal composition according to claim 6, wherein the adjuvant is a diluent.

* * * * *

UNITED STATES PATENT AND TRADEMARK OFFICE
CERTIFICATE OF CORRECTION

PATENT NO. : 5,776,965
DATED : July 7, 1998
INVENTOR(S) : Ki-Jun HWANG et al.

It is certified that error appears in the above-indentified patent and that said Letters Patent is hereby corrected as shown below:

On the title page,

Item [54], In the Title: Line 1, change "HAVING" to --HAVING A--.

Item [57], In the Abstract:    Line 2, change "having" to --having a--;

Line 11, change "by substituent" to --which is substituted by a substituent--;

Line 13, change "[0a8]alogen;" to --halogen;--;

Lines 15-16, change "by substituent" to --which is substituted by a substituent--;

Line 21, change "by substituent" to --which is substituted by a substituent--;

UNITED STATES PATENT AND TRADEMARK OFFICE
CERTIFICATE OF CORRECTION

PATENT NO.　：　5,776,965
DATED　　　：　July 7, 1998
INVENTOR(S)：　Ki-Jun HWANG  et al

It is certified that error appears in the above-identified patent and that said Letters Patent is hereby corrected as shown below:

In the Abstract:　　　Line 24, change "carbon" to -- a CH group --.

Signed and Sealed this

Thirteenth Day of October 1998

*Attest:*

*Attesting Officer*

BRUCE LEHMAN

*Commissioner of Patents and Trademarks*